United States Patent [19]

Thies et al.

[11] Patent Number: 4,714,709
[45] Date of Patent: Dec. 22, 1987

[54] N-(2,10-DIOXA-TRICYCLO-[5,3,1,0³,⁸]-UNDECANE-5-YL)-TRYPTAMINE DERIVATIVES AND MEDICAL COMPOSITIONS THEREOF

[75] Inventors: Peter W. Thies; Samuel David, both of Hanover; Ulrich Kuehl, Gehrden; Gerd Buschmann, Hanover; Peter Flecker, Bad Vilbel, all of Fed. Rep. of Germany

[73] Assignee: Kali-Chemie Pharma GmbH, Hanover, Fed. Rep. of Germany

[21] Appl. No.: 653,707

[22] Filed: Sep. 24, 1984

[30] Foreign Application Priority Data

Oct. 1, 1983 [DE] Fed. Rep. of Germany ....... 3335826

[51] Int. Cl.⁴ .................... A61K 31/40; C07D 405/12
[52] U.S. Cl. .................................. 514/414; 548/454
[58] Field of Search ................. 548/454; 514/414; 549/360; 564/459

[56] References Cited

U.S. PATENT DOCUMENTS

| | | | |
|---|---|---|---|
| 4,117,148 | 9/1978 | Thies et al. | 424/278 |
| 4,141,988 | 2/1979 | Thies et al. | 424/278 |
| 4,158,061 | 6/1979 | Thies et al. | 424/278 |
| 4,163,055 | 7/1979 | Thies et al. | 424/276 |
| 4,182,889 | 1/1980 | Asai et al. | 546/197 |
| 4,207,331 | 6/1980 | Thies et al. | 424/278 |
| 4,242,341 | 12/1980 | Thies et al. | 424/248.55 |
| 4,526,991 | 7/1985 | Thies et al. | 549/360 |

FOREIGN PATENT DOCUMENTS 2129507 12/1972 Fed. Rep. of Germany .

Primary Examiner—Glennon H. Hollrah
Assistant Examiner—D. B. Springer
Attorney, Agent, or Firm—Schwartz, Jeffery, Schwaab, Mack, Blumenthal & Evans

[57] ABSTRACT

N-(2,10-dioxa-tricyclo-[5,3,1,0³,⁸]-undecane-5-yl)-tryptamine compounds corresponding to the formula

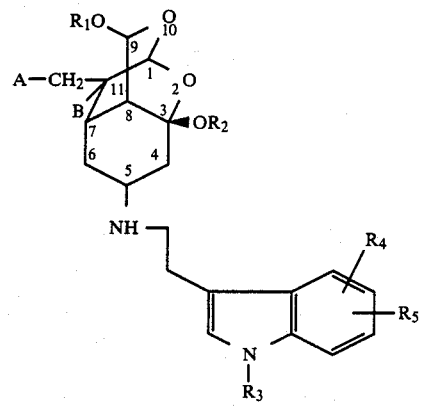

with blood-pressure lowering effects, a method of producing such compounds and pharmaceutical compositions incorporating such compounds, wherein $R_1$ is hydrogen, a benzyl or lower alkyl group; $R_2$ is a lower alkyl or lower alkanoyl group; $R_3$ is hydrogen or a lower alkyl group; $R_4$ is hydrogen, benzyloxy, hydroxy or a lower alkoxy group; $R_5$ is hydrogen, benzyloxy, hydroxy or a lower alkoxy group; and A and B either are both hydrogen or together represent a bond between their respective carbons.

16 Claims, No Drawings

N-(2,10-DIOXA-TRICYCLO-[5,3,1,0³,⁸]-UNDECANE-5-yl)-TRYPTAMINE DERIVATIVES AND MEDICAL COMPOSITIONS THEREOF

BACKGROUND OF THE INVENTION

The present invention relates to new N-(2,10-dioxa-tricyclo-[5,3,1,0³,⁸]-undecane-5-yl-tryptamine compounds and their salts, as well as the preparation of pharmaceuticals which contain these compounds, and a process for producing these compounds.

It has been found that the N-(2,10-dioxa-tricyclo-[5,3,1,0³,⁸]-undecane-5-yl-tryptamine compounds according to the invention have valuable pharmacological properties, particularly blood pressure lowering effects. These compounds possess an advantageous activity profile with a good therapeutic range and low toxicity. Because of their effects, these new compounds are particularly suited for use as drugs in the treatment of high blood pressure.

SUMMARY OF THE INVENTION

It is therefore an object of the present invention to develop new drugs which have beneficial effects on the cardiovascular system.

It is specifically an object of the present invention to produce new N-(2,10-dioxa-tricyclo-[5,3,1,0³,⁸]-undecane-5-yl)-tryptamine compounds with valuable pharmacological properties, particularly blood pressure lowering properties.

In accomplishing the foregoing objects, there have been provided in accordance with the present invention N-(2,10-dioxa-tricyclo-[5,3,1,0³,⁸]-undecane-5-yl)-tryptamine compounds corresponding to Formula I

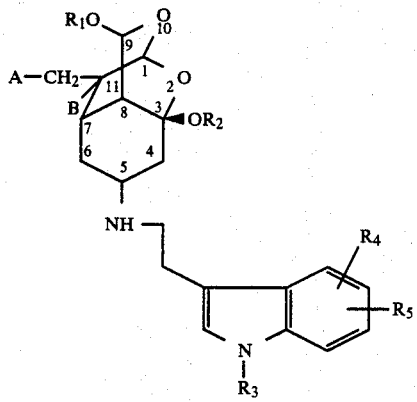

wherein $R_1$ is hydrogen, a lower alkyl group, or a benzyl group; $R_2$ is a lower alkyl or lower alkanoyl group; $R_3$ is hydrogen or a lower alkyl group; $R_4$ is hydrogen, a lower alkoxy group, a benzyloxy or a hydroxy group; $R_5$ is hydrogen, a lower alkoxy group, a benzyloxy group, or a hydroxy group; and A and B either are each hydrogen or together represent a bond between their respective carbons, and pharmaceutically acceptable salts of such compounds.

Also in accordance with the present invention, there has been provided a method of producing a compound of Formula I, comprising reacting a 2,6-dioxa-bicyclo-[2,2,2]-octane-7-yl-acetaldehyde of the Formula II

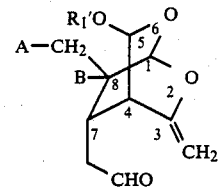

wherein A and B have the above-defined meaning and $R_1'$ is a benzyl or lower alkyl group, with an amine of Formula III

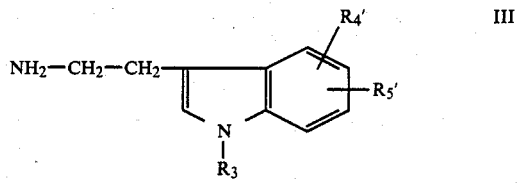

wherein $R_3$ has the above-defined meaning and $R_4'$ and $R_5'$ have meanings identical to those given above for $R_4$ and $R_5$ with the exception of hydroxy groups, in the presence of a solvent of Formula IV $$R_2OH \qquad \qquad IV$$

wherein $R_2$ has the above-defined meaning to produce a compound corresponding to Formula Ia

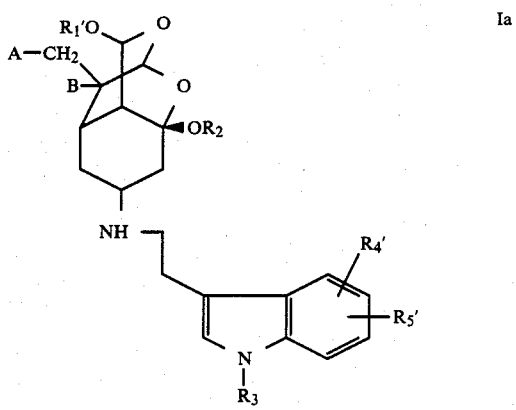

wherein A, B, $R_1'$, $R_2$, $R_3$, $R_4'$ and $R_5'$ all have the above-defined meanings.

Thereafter, any benzyloxy groups may be hydrogenolyzed to hydroxy groups and/or the resulting acid addition salt or free base of the compound of Formula I may be converted to the desired form, either free base or acid addition salt, respectively.

Also in accordance with the present invention, there has been provided a pharmaceutical composition comprising a pharmacologically effective quantity of the compound of Formula I, and either conventional auxiliary substances or carrier substances or both.

Further objects, features and advantages of the present invention will become apparent from the following detailed description of preferred embodiments.

DESCRIPTION OF PREFERRED EMBODIMENTS

The present invention relates to new compounds corresponding to the general Formula I, wherein $R_1$ is hydrogen, a benzyl group or a lower alkyl group; $R_2$ is a lower alkyl or alkanoyl group; $R_3$ is hydrogen or a lower alkyl group; $R_4$ is hydrogen, a benzyloxy, hydroxy, or lower alkoxy group; $R_5$ is hydrogen, benzyloxy, hydroxy, or lower alkoxy group; and A and B either are each hydrogen or together represent a bond between their respective carbons. The present invention also relates to the acid addition salts of these compounds.

The lower alkyl groups in the residues $R_1$ to $R_5$ in compounds of Formula I may have branched or straight chains with preferably one to four carbons, particularly one or two carbon atoms. The residue $R_1$ is preferably lower alkyl, in particular, a methyl group. The residue $R_2$ is preferably a lower alkyl (for instance, methyl, ethyl, n-propyl, isopropyl, n-butyl, or tert-butyl), or a lower alkanoyl group such as an acetyl group. The residues $R_3$, $R_4$ and $R_5$ are preferably hydrogen. If $R_3$ is an alkyl group, then it is preferably a methyl group. If either $R_4$ or $R_5$, or both, represent a lower alkoxy group, then they are preferably methoxy groups.

In compounds of Formula I, the substituents on asymetric centers $C_5$, $C_9$ and $C_{11}$ of the 2,10-dioxatricyclo-[5,3,1,0$^{3,8}$]-undecane skeleton can be either in the R or S configuration, so that the compounds can be present in several diastomeric forms. If A and B are both hydrogen, then $C_{11}$ is preferably in the R configuration. $C_9$ is preferably in the R configuration.

The present invention comprises all diastomeric forms of compounds of Formula I which result through variation of configuration at asymmetric centers $C_5$, $C_9$ and $C_{11}$.

According to the invention, new N-(2,10-dioxatricyclo-[5,3,1,0$^{3,8}$]-undecane-5-yl)-tryptamine compounds of Formula I and their salts are produced by reacting compounds of the general Formula II with amines of the general Formula III in the presence of a nucleophilic solvent of the general Formula IV. In Formula II, A and B have the above meanings, and $R_1'$ is either a benzyl or lower alkyl group. In Formula III, $R_3$ has the above meaning and $R_4'$ and $R_5'$ represent the same groups as $R_4$ and $R_5$, with the exception of hydroxy. In Formula IV, $R_2$ has the above meaning. In the resulting compound of the general Formula Ia, wherein A, B, $R_1'$, $R_2$, $R_3$, $R_4'$ and $R_5'$ have the above meanings, all benzyloxy groups may be cleaved to hydroxy groups by hydrogenolysis, if desired. Where appropriate, compounds of Formula Ia can be converted to the acid addition salts of free base compounds of Formula I, or the acid addition salts can be converted to free base compounds of Formula I.

The cyclization reaction according to the invention of an aldehyde of Formula II with an amine of Formula III and a nucleophile of Formula IV can be understood as a two-step reaction, the steps of which take place simultaneously or one after the other. The first step is a condensation reaction of the aldehyde of Formula II with the amine of Formula III with formation of an imine. The second step consists of an attack of the nucleophile of Formula IV on the exocyclic enol-ether of Formula II, with subsequent cyclization with the addition of a molecule of Formula IV.

The second step is, in the interest of expendiency, promoted by proton catalysis. Provided that the nucleophile of Formula IV is an acid, it can also function as an acid catalyst. If an alcohol is used as the nucleophile of Formula IV, it is appropriate to use the amine of Formula III in the form of an acid addition salt, such as a hydrochloride, or to add a catalytic quantity of an inorganic acid.

According to the invention, the reaction of the aldehyde of Formula II with the amine III in the nucleophylic solvent of Formula IV is conducted at temperatures between room temperature and about 100° C., preferably between about 40° and 80° C. The solvent may be the nucleophilic solvent IV alone or a mixture with additional inert aprotic organic solvents, for example, aromatic hydrocarbons such as benzene or toluene, open-chain ethers or cyclic ethers such as dioxane. If desired, the reaction of the aldehyde of Formula II with the amine of Formula III can be conducted in the above mentioned inert aprotic solvent, and the resulting reaction mixture subsequently treated with nucleophilic solvent of Formula IV.

All benzyloxy groups present can be cleaved by hydrogen to hydroxy groups in a known manner, for example, in the presence of a palladium/carbon catalyst.

The configurations of all the asymetric centers of compounds of Formula II are maintained in the cyclization reaction with amines of Formula III and nucleophiles of Formula IV. The configurations of substituents on asymmetric centers $C_9$ and $C_{11}$ in compounds of Formula I are therefore identical to the configurations on corresponding carbons on the starting product. A mixture of 5S and 5R diastereomers results from the cyclization. The ratio of diastereomers can vary with the choice of nucleophiles of Formula IV, but generally a majority of the 5S diasteromer is formed. The two diastereomers may be separated by chromatography of the crude product because of their differeing polarities, and each later isolated.

Compounds of Formula I, made by the process according to the invention, can be isolated and purified in a known manner as acid addition salts or free bases. Acid addition salts can be converted to free bases in the conventional manner and the free bases subsequently converted to pharmacologically acceptable acid addition salts in an also known manner.

Pharmacologically acceptable acid addition salts of compounds of Formula I include, for example, salts with hydrochloric acid, hydrobromic acid, phosphoric acid, methane sulfonic acid, benzene sulfonic acid, para-toluene sulfonic acid, citric acid, acetic acid, lactic acid, succinic acid, maleic acid, fumaric acid, malic acid, tartaric acid, benzoic acid, phenylacetic acid or mandelic acid.

The starting compounds of Formula II can be obtained by treating compounds of the general Formula V

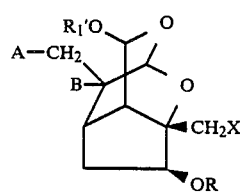

with a base in the presence of a solvent. In Formula V, $R_1$, A and B have the aforesaid meanings, X is iodine or bromine and R is hydrogen or a lower acyl group. Preferably, compounds of Formula V are reacted where X is iodine and R is acetyl or hydrogen. Compounds of Formula V, wherein R is hydrogen, can be formed by hydrolysis of compounds of Formula V in which R is an acetyl group.

Appropriate bases for treating compounds of Formula V include alkali metal alkoxides such as sodium methylalcoholate, alkali metal hydroxides, alkali metal carbonates such as potassium carbonate, or alkali metal hydrides such as sodium hydride. Additionally, quaternary organic ammonium hydroxides such as quaternary lower-alkyl ammonium hydroxides like t-butyl ammonium hydroxide, or tertiary organic amines may also be used.

The reaction is carried out in an appropriate solvent in which both compounds of Formula V and the bases used are soluble. Examples of appropriate solvents include lower alcohols such as methanol or ethanol; cyclical or open ethers such as diethyl ether, tetrahydrofuran or dioxane; or aromatic hydrocarbons such as toluene or benzene. If necessary, these solvents may be used mixed with water. In case bases such as alkali metal alcoholates are used, the preferred solvents would be lower alcohols.

The reaction can be conducted between about 10° C. and about 110° C., preferably between room temperature and about 80° C. The reaction may take between 1 and 5 hours to complete, depending on the starting material and on the reaction conditions. In case a compound of Formula IV is chosen in which R is an acyl group, the base used, the quantity of base, and the reaction conditions must, of course, be chosen for a hydrolysis of the ester group. The starting compounds of Formula V and their production are known from, for example, from U.S. Pat. Nos. 4,163,055; 4,158,061; 4,182,889; 4,207,331; and 4,242,341, the entire disclosures of which are incorporated herein by reference and from German Offenlegungsschrift No. 21 29 507. These compounds can be produced by the methods described in the above publications, or by methods analogous to the methods described therein. Compounds of Formula V, where A and B each represent a hydrogen, can be formed by hydrogenation of compounds of Formula V wherein A and B together represent a bond between their respective carbons. The hydrogenation reaction produces a mixture of diastereomers in which the R and S configurations are present in the ratio of 9:1. The diastereomers can be separated by fractional crystallization as described in U.S. Pat. No. 4,182,889.

The starting tryptamine compounds of Formula III are known, or can be produced by known methods for the production of substituted tryptamines. Trypamine compounds of Formula III can, for example, be produced starting with indols of Formula VI,

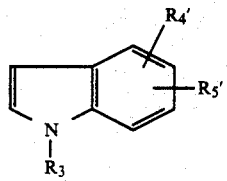
VI wherein $R_3$, $R_4'$ and $R_5'$ have the above meanings. Indoles of Formula VI are converted to the corresponding 3-dimethylaminomethyl indoles by a Mannich reaction with formaldehyde and dimethylamine. The product is then quaternized by reaction with methyl iodide, and the quaternary 3-trimethylammonim methyl indole product is reacted with alkali metal cyanide to produce the corresponding indole-3-yl-acetonitrile. The latter is reduced to a tryptamine of Formula III.

The Mannich reaction can be conducted with a 37% formaldehyde solution and dimethylamine in a dioxane/water mixture with the addition of glacial acetic acid. The subsequent quaternization is preferably done with methyl iodide in ethanol at 0° C. Sodium cyanide or potassium cyanide is suitable for use as the alkali metal cyanide. The reaction of the quaternary product with cyanide is preferably conducted in an alcohol/water mixture at an elevated temperature, for example, 80° C. Hydride catalysts may be used for reducing the acetonitriles. Suitale catalyts include lithium aluminum hydride in tetrahydrofuran at about 65° C. or diisobutyl aluminum hydride in methylene chloride at about room temperature.

Indoles of Formula VI, wherein $R_3$ is a lower-alkyl group, can be produced in a known manner by alkylation of the corresponding 1-position of unsubstituted indoles with alkyl halides or alkyl sulfonic acid esters.

Compounds of Formula I according to the invention and their pharmacologically acceptable salts are characterized by interesting pharmacological properties. They advantageously affect the cardiovascular system and possess a high physiological tolerability. The compounds specifically exhibit a marked blood pressure lowering effect, while only insignificantly affecting the heart rate. The cardiovascular effects of substances of Formula I can be demonstrated by standard pharmacological test methods on animals.

The effect of the substances on blood pressure, heart rate and EKG parameters during continuous i.v. infusion on anesthetized rats is determined by the method of Buschmann et al, Journal of Cardiovascular Pharmacology, Vol. 2, pp. 777–781 (1980). Male Wistar rats having a body weight of 330 to 370 grams are anesthetized with an i.p. application of 1.25 g/kg of urethane and tracheotomized. After an equilibration phase of 10 minutes, measurements are begun. Initial values are measured in a predrug phase of 5 minutes. Thereafter, the test substances are applied intravenously as a continuous infusion in isotonic sodium chloride solution, beginning with a dosage of 0.01 μmol/kg/min. The dosage is increased by a factor of 10 every 10 minutes without increase in the infusion volume. The mean blood pressure ($P_m$) is calculated from measurements of the systolic and diastolic blood pressures ($P_{syst}$ and $P_{diast}$). The following values are taken from the electrocardiogram (EKG): the atrioventricular conduction time (in milliseconds, corrected for changes in heart rate=$PR_c$); the time interval of intraventricular excitation (QRS); and the period of time from the beginning of the ventricular excitation to a maximum of the T-wave (R-αT). The heart rate is determined from the R-R interval. From the measured blood pressure and the heat rate parameters the respective $ED_{75}$ values in μmol/kg are calculated. This represents the total dosage which brings about a 25% reduction in a particular parameter with respect to the predrug value. From the EKG parameters the respective $ED_{125}$ values are calculated. The $ED_{125}$ is the total dosage which increases the respective parameters by 25% by their predrug values. The minimum lethal dose ($DL_{min}$) in μmol/kg is also determined in the experiment. In the aforedescribed experimental set-up, compounds of Formula IV exhibit blood pressure lowering effects in the dosage range from between 1 to 100 μmol/kg. For example, the following values were ascertained for the compounds in Examples 1a, 2a and 3a, respectively:

| Substance (Example No.) | | 1A | 2A* | 3A*+ |
|---|---|---|---|---|
| Heart rate $ED_{75}$ | μmol/kg | 41 | 21 | 100 |
| $P_{syst}$ $ED_{75}$ | μmol/kg | 21 | 6.7 | 70 |
| $P_{diast}$ $ED_{75}$ | μmol/kg | 5.9 | 3.9 | 30–35 |
| $P_m$ $ED_{75}$ | μmol/kg | 9.7 | 4.5 | 40 |
| $PR_c$ $ED_{125}$ | μmol/kg | 93 | 42 | 40 |
| QRS $ED_{125}$ | μmol/kg | 35 | 28 | 45 |
| R-αT $ED_{125}$ | μmol/kg | 19 | 6.7 | 20 |
| $DL_{min}$ | μmol/kg | 210 | 100 | 210 |

*addition of solubilizer
+the solubilizer itsef shows a weak, blood pressure increasing effect in higher dosages.

It is evident from these values that the compounds according to the invention have a highly specific blood pressure lowering effect, particularly on the diastolic blood pressure, and are highly tolerable. Because of their specific blood pressure lowering properties, these substances are suited for use as antihypertensive drugs for the treatment of high blood pressure.

The compounds of Formula I and their physiologically acceptable salts can be used as medicines in combination with conventional pharmaceutical carriers, and-/or auxiliary substances, in galenic preparations such as tablets, capsules, suppositories or solutions. These galenic preparations can be produced by known methods using conventional carrier substances such as milk sugar, starch, talc, or liquid diluting substances such as water, fatty oils, or liquid paraffins.

The following examples are intended to further explain the invention, but are not intended to limit its scope.

STARTING MATERIAL EXAMPLE A

Production of the starting compound, 1R,4S,5R,7R-5-methoxy-3,8-dimethylene-2,6-dioxa-bicyclo-[2,2,2]-octane-7-yl-acetaldehyde.

A solution of 7.6 g 1R,3S,4S,6R,7S,8R-3-iodomethyl-4-acetoxy-8-methoxy-10-methylene-2,9-dioxa-tricyclo[4,3,1,0$^{3,7}$]-decane in 100 ml of absolute methanol is added to a sodium methylate solution made by dissolving 0.44 g of sodium in 40 ml of absolute methanol. The mixture is allowed to react at 60° C. for 4.5 hours and then is worked up as follows. It is poured into ice water, well salted out with sodium chloride, and extracted with ether. A few drops of glacial acetic acid are added to the ether phase, it is dried over sodium sulfate, filtered, and the solvent removed. The residue is 4.29 g of crude 1R,4S,5R,7R-5-methoxy-3,8-dimethylene-2,6-dioxa-bicyclo-[2,2,2]-octane-7-yl-acetaldehyde.

The crude product can be used in this form as an intermediate in the reaction to produce a compound of Formula I.

The crude product can be purified by chromotography with silica gel, using n-hexane/ether as the elution solvent. After the removal of solvent from the eluate, the resulting product, which is pure according to thin layer chromatographic analysis, can be crystallized out of n-hexane/ether. The 1R,4S,5R,7R-5-methoxy-3,8-dimethylene-2,6-dioxa-bicyclo-[2,2,2]-octane-7-yl-acetaldehyde produced has the following physical characteristics:

melting point: 56° to 59° C.

IR-spectrum: 3070 cm$^{-1}$, 1725 cm$^{-1}$, 1675 cm$^{-1}$, 1170 cm$^{-1}$, 1075 cm$^{-1}$, 960 cm$^{-1}$ (B) Six grams of 1R,3S,4S,6R,7S,8R-3-iodomethyl-4-acetoxy-8-methoxy-10-methylene-2,9-dioxa-tricyclo[4,3,1,0$^{3,7}$]-decane are added to a sodium methylate solution made by dissolving 2.5 g of sodium in 250 ml of absolute methanol and the reaction mixture is stirred at a bath temperature of 60° C. for 1.5 hours under nitrogen and then is worked up as follows. The volume of the solution is reduced to one quarter of its original volume by rotary evaporation. To the concentrated solution is added 100 g of saturated ammonium sulfate solution, whereby NH$_3$ is evolved. Thereafter, the resulting solution is extracted 5 times with a total volume of 500 ml ether. The ether extracts are washed with 50 ml of sodium sulfate solution and with water; dried over magnesium sulfate, and evaporated. 2.9 g of crude 1R,4S,5R,7R-5-methoxy-3,8-dimethylene-2,6-dioxabicyclo-[2,2,2]-octane-7-yl-acetaldehyde results. This crude product can be utilized, without further purification, in the synthesis of compounds of Formula I. If desired, it can be further purified as described in Starting Material Example A:A). The purified product is identical to that obtained in Starting Material Example A:A)

STARTING MATERIAL EXAMPLE B

Production of the starting compound 1R,4S,5R,7R,8R-5-methoxy-8-methyl-3-methylene-2,6-dioxa-bicyclo-[2,2,2]-octane-7-yl-acetaldehyde.

(A) A solution of 10 g of 1R,3S,4S,6R,7S,8R,10R-3-iodomethyl-4-acetoxy-8-methoxy-10-methyl-2,9-dioxa-tricyclo[4,3,1,0$^{3,7}$]-decane in 220 ml of methanol is mixed with 3.6 g of potassium carbonate, and the resulting reaction mixture is stirred at room temperature for approximately 1 hour and then is worked up as follows. It is diluted with water and extracted with methylene chloride. The organic phase is separated, dried over sodium sulfate, filtered and the solvent removed under reduced pressure. As a result 8.7 g of 1R,3S,4S,6R,7S,8R,10R-3-iodomethyl-4-hydroxy-8-methoxy-10-methyl-2,9-dioxa-tricyclo-[4,3,1,0$^{3,7}$]-decane with a melting point of 92° to 93° C. are obtained.

(B) A solution of 3.24 g of the product of Starting Material Example B:A) in 50 ml of absolute methanol is mixed with a sodium methylate solution made by dissolving 0.23 g of sodium in 50 ml of absolute methanol. The reaction mixture is stirred for about 3 hours at a temperature of 60° C. Thereafter, the reaction mixture is worked up by pouring it into ice water, salting out well with sodium chloride, and extracting with ether. The ether phase is mixed with a few drops of glacial acetic acid, dried over sodium sulfate, filtered, and the solvent removed under reduced pressure. The residue is 2.7 g of crude 1R,4S,5R,7R,8R-5-methoxy-8-methyl-3-methylene-2,6-dioxa-bicyclo-[2,2,2]-octane-7-yl-acetaldehyde. This crude product can be used, without any further purification, as an intermediate in the synthesis of compounds of Formula I.

STARTING MATERIAL EXAMPLE C

Production of the starting compound 1R,4S,5R,7R-5-benzyloxy-3,8-dimethylene-2,6-dioxa-bicyclo-[2,2,2]-octane-7-yl-acetaldehyde.

Eight and one-half grams of 1R,3S,4S,6R,7S,8R-3-iodomethyl-4-acetoxy-8-benzyloxy-10-methylene-2,9-dioxa-tricyclo-[4,3,1,0$^{3,7}$]-decane are mixed with a sodium methylate solution made by dissolving 2.5 g of sodium in 300 ml of absolute methanol, as described in Starting Material Example A. The above starting material has a melting point of 69° to 70° C., and is synthesized in a known manner by reacting didrovaltratum with benzyl alcohol and hydroiodic acid. The reaction mixture is worked up as follows. It is poured onto ice water and extracted with methylene chloride. The organic phase is separated and further worked up as described in Starting Material Example A. The residue is 6 g of crude 1R,4S,5R,7R-5-benzyloxy-3,8-dimethylene-2,6-dioxa-bicyclo-[2,2,2]-octane-7-yl-acetalhyde. This product can be used directly as an intermediate in the synthesis of compounds of Formula I.

EXAMPLE 1

Synthesis of 1R,3R,5S,7R,8R,9R-N-(3,9-dimethoxy-11-methylene-2,10-dioxa-tricyclo-[5,3,1,0$^{3,8}$]-undecane-5-yl)tryptamine and 1R,3R,5R,7R,8R,9R-N-(3,9-dimethoxy-11-methylene-2,10-dioxa-tricyclo-[5,3,1,0$^{3,8}$]-undecane-5-yl)tryptamine.

(A) The 1R,4S,5R,7R-5-methoxy-3,8-dimethylene-2,6-dioxabicyclo-[2,2,2]-octane-7-yl-acetaldehyde obtained from 4 g of 1R,3S,4S,6R,7R,8R-3-iodomethyl-4-acetoxy-8-methoxy-10-methylene-2,9-dioxa-tricyclo-[4,3,1,0$^{3,7}$]-decane, according to the procedure of Starting Material Example A(B), is dissolved in 100 ml of absolute methanol. The resulting solution is mixed with 2 g of tryptamine hydrochloride under nitrogen, and the reaction mixture is stirred at a bath temperature of 60° C. for 3.5 hours and then is worked up by distilling off the methanol, alkalizing the remaining reaction mixture with concentrated sodium carbonate, and extracting with methylene chloride. The organic phase is dried over magnesium sulfate, and the solvent removed. The yield is 4 g of a red-colored crude product. The crude product is purified by column chromotography under pressure, using chloroform with 5% methanol as the elution solvent. The eluate yields 890 mg of nonpolar 1R,3R,5S,7R,8R,9R-N-(3,9-dimethoxy-11-methylene-2,10-dioxa-tricyclo-[5,3,1,0$^{3,8}$]-undecane-5-yl)-tryptamine as a colorless solid foam. The end product has the following physical characteristics:

$[\alpha]^{20}_D = +3.3°$ (C=1 in CH$_3$OH)

Molecular weight: calculated: 384.2049; found: 384.2048

Mass spectrum (130° C.): M$^+$=384(4), 383(11), 352(11), 253(43), 221(21), 192(27), 179(42), 175(9), 144(11), 131(100).

(B) In addition, the polar byproduct, crude 1R,3R,5R,7R,8R,9R-N-(3,9-dimethoxy-11-methylene-2,10-dioxatricyclo-[5,3,1,0$^{3,8}$]-undecane-5-yl)-tryptamine, is also obtained from the eluate. An additional purification by preparative thin layer chromotagraphy, using chloroform with 5% methanol as elution solvent, yields 125 mg of the purified product as a colorless solid foam. This product has the following physical characteristics:

Molecular weight: calculated: 384.2049; found: 384.2048

Mass spectrum (110° C.): M$^+$=384(7), 353(8), 254(100), 242(12), 222(27), 196(28), 166(38), 144(28), 130(52)

EXAMPLE 2

Synthesis of 1R,3R,5S,7R,8R,9R-N-(3-t-butoxy-9-methoxy-11-methylene-2,10-dioxa-tricyclo-[5,3,1,0$^{3,8}$]-undecane-5-yl)tryptamine and 1R,3R,5R,7R,8R,9R-N-(3-t-butoxy-9-methoxy-11-methylene-2,10-dioxa-tricyclo-[5,3,1,0$^{3,8}$]-undecane-5-yl)tryptamine.

(A) 580 mg of crude 1R,4S,5R,7R-5-methoxy-2,8-dimethylene-2,6-dioxa-bicyclo-[2,2,2]-octane-7-yl-acetaldehyde, produced in a manner analogous to that described in Starting Material Example A(B), are dissolved in a mixture of 10 ml of absolute dioxane and 30 ml of absolute t-butanol, to which are subsequently added 540 mg of tryptamine hydrochloride. The reaction mixture is stirred for 4 hours at a bath temperature of from 60° to 70° C. and then is worked up. The solvent is distilled off, and the remaining reaction mixture is alkalized with concentrated sodium carbonate solution and extracted with chloroform. The organic phase is dried over magnesium sulfate and the solvent removed. 1.1 g of crude product is obtained. This is purified by column chromatography under pressure, using chloroform with 5% methanol as the elution solvent. The eluate yields 270 mg of nonpolar 1R,3R,5S,7R,8R,9R-N-(3-t-butoxy-9-methoxy-11-methylene-2,10-dioxa-tricyclo[5,3,1,0$^{3,8}$]-undecane-5-yl)-tryptamine as a colorless solid foam. The product has the following physical characteristics:

$[\alpha]^{20}_D = -8°$ (C=1 in CH$_3$OH)

Mass spectrum (160° C.): M$^+$=426(1), 425(3), 395(1), 353(3), 339(4), 296(4), 222(57), 193(20), 180(73), 165(12), 144(19), 131(100)

(B) In addition, the polar byproduct, crude 1R,3R,5R,7R,8R,9R-N-(3-t-butoxy-9-methoxy-11-methylene-2,10-dioxa-tricyclo-[5,3,1,0$^{3,8}$]-undecane-5-yl)-tryptamine is also obtained from the eluate. An additional purification by preparative thin layer chromatography, using chloroform with 10% methanol as elution solvent, yields 34 mg of the purified product. This product has the following physical characteristics:

Mass spectrum (80° C.): M$^+$=426(3), 411(8), 406(6), 393(3), 333(100), 319(10), 302(21), 288(28), 226(19), 222(391).

EXAMPLE 3

Synthesis of 1R,3R,5S,7R,8R,9R-N-(3-acetoxy-9-methoxy-11-methylene-2,10-dioxa-tricyclo-[5,3,1,0$^{3,8}$]-undecane-5-yl)tryptamine and 1R,3R,5R,7R,8R,9R-N-(3-acetoxy-9-methoxy-11-methylene-2,10-dioxa-tricyclo-[5,3,1,0$^{3,8}$]-undecane-5-yl)tryptamine.

(A) Two and one-half grams of tryptamine are dissolved in 50 ml of a mixture of absolute toluene and dioxane in a ratio of 4:1 at a bath temperature of 100° C. and allowed to cool off. A solution of 2.5 g of crude 1R,4S,5R,7R-5-methoxy-3,8-dimethylene-2,6-dioxabicyclo-[2,2,2]-octane-7-yl-acetaldehyde in 20 ml of toluene is added to the above solution while the latter is still warm. The solution becomes turbid. 1 g of magnesium sulfate is added and the reaction mixture is stirred at room temperature for an additional 24 hours. Subsequently, the reaction mixture is filtered, and rinsed with methylene chloride. The methylene chloride is removed and the residue is allowed to stand in 50 ml dry, freshly distilled glacial acetic acid at room temperature for 12 hours under nitrogen. After careful removal of the solvent by distillation, the reaction mixture which remains in the water bath is alkalized with concentrated sodium carbonate solution and immediately extracted with methylene chloride. The organic phase is washed with water, dried over magnesium sulfate and the solvent removed. 4.9 g of crude product results. This is purified by column chromatography under pressure, using chloroform with 5 to 10% methanol as elution solvent. The eluate yields 710 mg of nonpolar 1R,3R,5S,7R,8R,9R-N-(3-acetoxy-9-methoxy-11-methylene-2,10-dioxatricyclo-[5,3,1,0$^{3,8}$]-undecane-5-yl)-tryptamine as a colorless solid foam. This product has the following physical characteristics:

$[\alpha]^{20}_D = +1.1°$ (C=1 in CH$_3$OH)

Molecular weight: calculated: 412.1998; found: 412.1992

Mass spectrum (130° C.): M$^+$ = 412(5), 381(3), 353(4), 321(4), 228(13), 222(36), 213(9), 210(8), 193(12), 180(43), 171(19), 165(10), 156(6), 148(11), 144(41), 131(100)

(B) In addition, the polar byproduct crude 1R,3R,5R,7R,8R,9R-N-(3-acetoxy-9-methoxy-11-methylene-2,10-dioxa-tricyclo-[5,3,1,0$^{3,8}$]-undecane-5-yl)-tryptamine, is also obtained from the more polar fractions of the eluate. An additional purification by preparative thin layer chromatography, using chloroform with methanol as the elution solvent, yields 105 mg of the purified product. This product has the following physical characteristics:

Molecular weight: calculated: 412.1998; found: 412.1996

Mass spectrum (160° C.): M$^+$ = 412(4), 381(2), 352(3), 321(3), 228(7), 222(42), 213(5), 210(8), 193(15), 180(40), 171(11), 165(9), 148(12), 144(37), 131(100).

EXAMPLE 4

Production of 1R,3R,5S,7R,8R,9R-N-(3,9-dimethoxy-11-methyl-2,10-dioxa-tricyclo-[5,3,1,0$^{3,8}$]-undecane-5-yl)-5'-methoxytryptamine and 1R,3R,5R,7R,8R,9R-N-(3,9-dimethoxy-11-methyl-2,10-dioxa-tricyclo-[5,3,1,0$^{3,8}$]-undecane-5-yl)-5'-methoxytryptamine.

Two and seven-tenths grams of 1R,4S,5R,7R,8R-5-methoxy-8-methyl-3-methylene-2,6-dioxa-bicyclo-[2,2,2]-octane-7-yl-acetaldehyde, produced according to Starting Material Example B, are dissolved in methanol and reacted with 1 g methoxytryptamine according to the procedure described in Example 1A. 1.3 g of crude product are obtained. This is purified by column chromatography as described in Example 1. The purified crude product is further purified by preparative thin layer chromatography, using methylene chloride with 20% methanol as the elution solvent. This last step results in 200 mg of purified 1R,3R,5S,7R,8R,9R-N-(3,9-dimethoxy-11-methyl-2,10-dioxa-tricyclo-[5,3,1,0$^{3,8}$]-undecane-5-yl)-5'-methoxytryptamine as a colorless solid foam. This product has the following physical characteristics:

$[\alpha]^{20}_D = -14.2°$ (C=1 in CH$_3$OH)

Mass spectrum (190° C.): M$^+$ = 416(3), 385(5), 256(15), 224(40), 216(12), 182(13), 174(29), 173(26), 168(16), 162(22), 161(100), 160(44), 161(100), 160(44).

The remaining product is obtained as a solid foam, which is a mixture of the 5S and 5R diastereomers.

EXAMPLE 5

Production of 1R,3R,5S,7R,8R,9R-N-(3,9-dimethoxy-11-methyl-2,10-dioxa-tricyclo-[5,3,1,0$^{3,8}$]-undecane-5-yl)-5'-benzyloxytryptamine One and two-tenths grams of 1R,4S,5R,7R,8R-5-methoxy-8-methyl-3-methylene-2,6-dioxa-bicyclo-[2,2,2]-octane-7-yl-acetaldehyde are dissolved in methanol and reacted with 1.0 g of 5-benzyloxytryptamine as described in Example 1A. The resulting crude product is purified by column chromotography as described in Example 1. 1.5 g of purified 1R,3R,5S,7R,8R,9R-N-(3,9-dimethoxy-11-methyl-2,10-dioxatricyclo-[5,3,1,0$^{3,8}$]-undecane-5-yl)-5'-benzyloxytryptamine are obtained as a colorless solid foam. This product has the following physical characteristics:

$[\alpha]^{20}_D = -30.2°$ (C=1 in CH$_3$OH)

Mass spectrum (190° C.): M$^+$ = 492(3), 461(6), 292(15), 256(17), 238(34), 237(100), 236(18), 224(43), 167(13), 146(56), 145(13), 91(29).

EXAMPLE 6

Synthesis of 1R,3R,5S,7R,8R,9R-N-(3-methoxy-9-benzyloxy-11-methylene-2,10-dioxa-tricyclo-[5,3,1,0$^{3,8}$]-undecane-5-yl)-tryptamine and 1R,3R,5R,7R,8R,9R-N-(3-methoxy-9-benzyloxy-11-methylene-2,10-dioxa-tricyclo-[5,3,1,0$^{3,8}$]-undecane-5-yl)-tryptamine.

Six grams of 1R,4S,5R,7R-5-benzyloxy-3,8-dimethylene-2,6-dioxa-bicyclo-[2,2,2]-octane-7-yl-acetaldehyde, produced as described in Starting Material Example C, are dissolved in 100 ml of methanol. 3.6 g of tryptamine are added to this solution in several portions. The reaction mixture is stirred for 2 hours at 60° C. Thereafter, the solvent is removed to dryness under reduced pressure. The residue is the crude hydrochloride of the diastereomer mixture of the title compounds. This mixture is separated by column chromatography over silica gel. The elution solvent is n-hexane with an increasing proportion of methylene chloride (up to 100%) followed by methylene chloride with increasing amounts of methanol (up to 5%). A first elution fraction yields 0.57 g of only slightly impure 1R,3R,5S,7R,8R,9R-N-(3-methoxy-9-benzyloxy-11-methylene-2,10-dioxa-tricyclo-[5,3,1,0$^{3,8}$]-undecane-5-yl)-tryptamine. This is again purified over silica gel with methylene chloride and up to 5% methanol as elution solvent. 0.33 g of purified 5S diastereomer is obtained as a solid foam. This product has the following optical rotation:

$[\alpha]^{20}_D = -22.1°$ (C=1 in CH$_3$OH)

The hydrochloride is converted to the free base by dissolving the salt in dichloromethane and reacting with one equivalent of barium hydroxide (BA(OH)$_2$.8H$_2$O). The reaction mixture is stirred at room temperature for 30 minutes, dried with sodium sulfate and filtered. Thereafter, the solvent is removed under reduced pressure. The free base is obtained as a solid foam with the following physical characteristics:

$[\alpha]^{20}_D = 18.3$ (C=1 in CH$_3$OH)

Mass spectrum (190° C.) M$^+$ = 460(0.6), 423(0.6), 330(16), 298(26), 144(14), 132(14), 131(95), 130(28), 95(7), 92(10), 91(100), 77(6)

In addition, a second, more polar fraction of the above eluate yields 1.7 g of an about 80% 5S and about 20% 5R diastereomer mixture. A third, still more polar fraction of the eluate yields 2.8 g of a crude diastereomer mixture containing the 5S and 5R diastereomers in approximately equal proportion. These diastereomer mixtures can, if desired, be separated by preparative thin layer chromatography into the two diastereomers.

EXAMPLE 7

Production of 1R,3R,5S,7R,8R,9R-N-(3-methoxy-9-isobutyloxy-11-methylene-2,10-dioxa-tricyclo-[5,3,1,0$^{3,8}$]-undecane-5-yl]-tryptamine and 1R,3R,5R,7R,8R,9R-N-(3-methoxy-9-isobutyloxy-11- methylene-2,10-dioxa-tricyclo-[5,3,1,0$^{3,8}$-undecane-5yl)-tryptamine

Eleven grams of crude 1R,4S,5R,7R-5-isobutyloxy-3,8-dimethylene-2,6-dioxa-bicyclo-[2,2,2]-octane-7-yl-acetaldehyde are dissolved in 200 ml of methanol. A total of 8 g of tryptamine hydrochloride is added to this solution in several increments. The reaction mixture is stirred for 3 hours at a bath temperature of 60° C. The starting material is produced analogously to Starting Material Example 3 by ring cleavage of 1R,3S,4S,6R,7S,8R-3-iodomethyl-4-acetoxy-8-isobutyloxy-10-methylene-2,9-dioxa-tricyclo-[4,3,1,0$^{3,7}$]-decane (melting point 45° to 50° C.) which in turn is produced by reaction of didrovaltratum with isobutyl alcohol and hydroiodic acid. The reaction mixture is subsequently worked up according to the procedure of Example 6. 3.2 g of 1R,3R,5S,7R,8R,9R-N-(3-methoxy-9-isobutyloxy-11-methylene-2,10-dioxa-tricyclo-[5,3,1,0$^{3,8}$]-undecane-5-yl)-tryptamine hydrochloride, containing little of the 5R diastereomer, are obtained from the first elution fraction. This compound is further purified over silica gel, using methylene chloride with up to 4% methanol as elution solvent. 1.3 g of purified product are obtained. After recrystalization from methylene chloride/n-hexane, 0.6 g of purified 5S diastereomer are obtained with a melting point of 205° to 209° C. This product has the following optical rotation:

$[\alpha]^{20}_D = -16.8°$ (C=1 in CH$_3$OH)

The hydrochloride can be converted to the free base in the form of a solid foam as described in Example 6. The free base has the following optical rotation:

$[\alpha]^{20}_D - 13.0°$ (C=1 in CH$_3$OH)

Additionally, 6.5 g of a crude hydrochloride of a mixture of the 2 diastereomers can be obtained from a second, more polar fraction of the above eluate, in which the 5S and the 5R diastereomers are present in approximately equal proportion.

EXAMPLE 8

Production of 1R,3R,5S,7R,8R,9R-N-(3-methoxy-9-hydroxy-11-methylene-2,10-dioxa-tricyclo-[5,3,1,0$^{3,8}$]-undecane-5-yl)-tryptamine Six-tenths grams of 1R,3R,5S,7R,8R,9R-N-(3-methoxy-9-benzyloxy-11-methylene-2,10-dioxa-tricyclo-[5,3,1,0$^{3,8}$]-undecane-5-yl)-tryptamine are dissolved in 15 ml of methanol and mixed with a soluton of 0.3 ml of concentrated hydrochloric acid in 5 ml of methanol. Thereafter, 0.215 g of a palladium catalyst (5% palladium/carbon) is added and the mixture hydrogenated at room temperature for 2 hours under 3 bar of hydrogen. After completion of the hydrogen up-take, the catalyst is filtered out, and all solvent removed from the filtrate under vacuum. 0.58 g of 1R,3R,5S,7R,8R,9R-N-(3-methoxy-9-hydroxy-11-methylene-2,10-dioxa-tricyclo-[5,3,1,0$^{3,8}$]-undecane-5-yl)-tryptamine, which is pure by thin-layer chromatographic analysis, is obtained as a solid foam. This product has the following optical rotation:

$[\alpha]^{24}_D = -23°$ (C=1 in CH$_3$OH)

EXAMPLE 9: PRODUCTION OF TABLETS

Tablets are produced with the following composition per tablet:

| | |
|---|---|
| 1R,3R,5S,7R,8R,9R-N—(3,9-dimethoxy-11-methylene-2,10-dioxa-tricyclo-[5,3,1,0$^{3,8}$]-undecane-5-yl)-tryptamine | 10 mg |
| Microcyrstalline cellulose (Avicell ® PH101) | 93 mg |
| Highly disperse silicic acid (Aerosil ® R972) | 12.5 mg |
| Carboxymethylcellulose (Tylose ®) | 7 mg |

The active ingredient is dissolved in with methylene chloride. The microcrystalline cellulose and highly disperse silicic acid are mixed and triturated with the solution of active ingredient. The resulting triturate is dried and then moistened with an aqueous solution of Tylose. The resulting granules are pressed through a 2 mm mesh screen, dried in a fluid bed dryer at 40°–45° C. and pressed through a 1.5 mm mesh screen. Thereafter, the following auxilliary substances are added:

| | |
|---|---|
| Cross-linked Polyvinyl pryrolidone (Crospovidone USP20/NF153) | 4.5 mg |
| Magnesium stearate | 1.5 mg |
| Highly disperse silicic acid | 1.5 mg |

The final mixture is then pressed into tablets of 130 mg.

The foregoing description has been set forth merely to illustrate the invention and is not intended to be limiting. Since modifications of the described embodiments incorporating the spirit and substance of the invention may occur to persons skilled in the art, the scope of the invention should be limited solely with respect to the appended claims and equivalents.

What is claimed is:

1. A compound corresponding to the formula

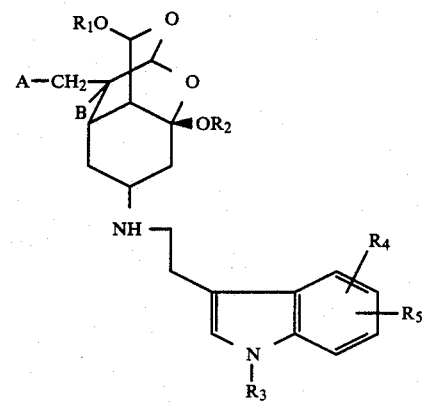

wherein
R$_1$ is hydrogen, a C$_1$-C$_4$ lower alkyl group, or a benzyl group;
R$_2$ is a C$_1$-C$_4$ lower alkyl or lower alkanoyl group;
R$_3$ is hydrogen or a C$_1$-C$_4$ lower alkyl group;
R$_4$ is hydrogen, a C$_1$-C$_4$ lower alkoxy group or a hydroxy group;
R$_5$ is hydrogen, a C$_1$-C$_4$ lower alkoxy group, or a hydroxy group;
and A and B either are each hydrogen or together represent a bond between their respective carbons and pharmaceutically acceptable acid addition salts thereof.

2. A compound according to claim 1, wherein R$_1$ is a lower alkyl group.

3. A compound according to claim 2, wherein R$_3$ is hydrogen.

4. A compound according to claim 3, wherein $R_1$ and $R_2$ are lower alkyl groups; and wherein $R_3$, $R_4$ and $R_5$ are all hydrogen.

5. A compound according to claim 1, wherein A and B together represent a single bond between their respective carbons.

6. A compound according to claim 5, wherein $R_1$ and $R_2$ are lower alkyl groups and $R_3$, $R_4$ and $R_5$ are hydrogen.

7. A compound according to claim 6, wherein $R_1$ and $R_2$ are methyl groups.

8. A compound according to claim 6, wherein $R_1$ is a methyl group and $R_2$ is a t-butyl group.

9. A compound according to claim 1, wherein $R_1$ is a methyl group, $R_2$ is an acetyl group and A and B together represent a bond between their respective carbons.

10. A compound according to claim 1, wherein $R_1$ and $R_2$ are methyl groups, A and B represent a bond between their respective carbons, and $R_5$ is a methoxy group.

11. A compound according to claim 1, wherein $R_1$ is a benzyl group, $R_2$ is a methyl group, and A and B represent a bond between their respective carbons.

12. A compound according to claim 1, wherein $R_1$ is an isobutyl group, $R_2$ is a methyl group, and A and B together represent a bond between their respective carbons.

13. A compound according to claim 1, wherein $R_1$ is a hydroxy group, $R_2$ is a methyl group, and A and B together represent a bond between their respective carbons.

14. A pharmaceutical composition comprising a pharmacologically effective amount of a compound corresponding to the formula:

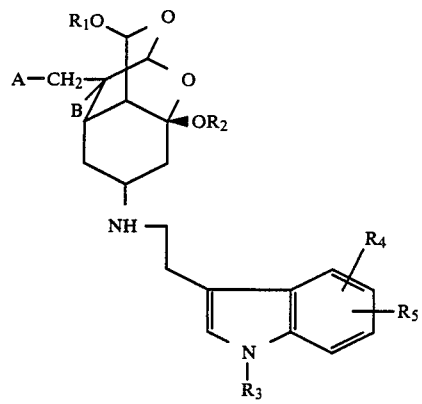

wherein
$R_1$ is hydrogen, a $C_1$–$C_4$ lower alkyl group, or a benzyl group;
$R_2$ is a $C_1$–$C_4$ lower alkyl or lower alkanoyl group;
$R_3$ is hydrogen or a $C_1$–$C_4$ lower alkyl group;
$R_4$ is hydrogen, a $C_1$–$C_4$ lower alkoxy group or a hydroxy group;
$R_5$ is hydrogen, a $C_1$–$C_4$ lower alkoxy group, or a hydroxy group; and at least one additional substance selected from the group consisting of conventional pharmaceutical carriers and auxilliary substances.

15. A compound corresponding to the formula

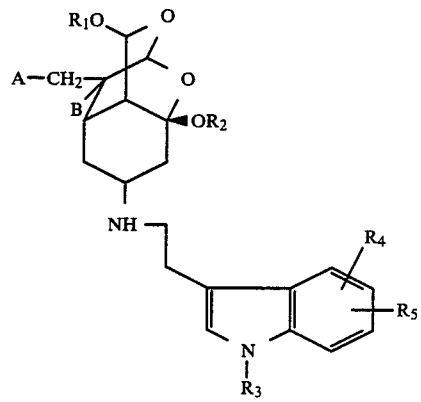

wherein
$R_1$ is hydrogen, a $C_1$–$C_4$ lower alkyl group, or a benzyl group;
$R_2$ is a $C_1$–$C_4$ lower alkyl or lower alkanoyl group;
$R_3$ is hydrogen or a $C_1$–$C_4$ lower alkyl group; one of $R_4$ and $R_5$ is a benzyloxy group, and the other of $R_4$ and $R_5$ is hydrogen, a $C_1$–$C_4$ lower alkoxy group, a benzyloxy group, or a hydroxy group;
and A and B either are each hydrogen or together represent a bond between their respective carbons and pharmaceutically acceptable acid addition salts thereof.

16. A compound according to claim 15, wherein $R_1$ and $R_2$ are methyl groups, A and B represent a bond between their respective carbons, and $R_5$ is a benzyloxy group.

* * * * *